United States Patent [19]

Oppenlander

[11] 4,395,921
[45] Aug. 2, 1983

[54] ADJUSTABLE VOLUME LIQUID DISPENSER

[75] Inventor: Jon E. Oppenlander, Lafayette, Calif.

[73] Assignee: Scientific Manufacturing Industries, Inc., Emeryville, Calif.

[21] Appl. No.: 277,902

[22] Filed: Jun. 26, 1981

[51] Int. Cl.³ .............................................. B01L 3/02
[52] U.S. Cl. .................................. 73/864.18; 222/43; 222/309
[58] Field of Search ..................... 222/41, 43, 46, 305, 222/32–35, 309; 73/864.18, 864.16

[56] References Cited

U.S. PATENT DOCUMENTS

| | | | |
|---|---|---|---|
| 2,771,217 | 11/1956 | Brown et al. | 222/43 |
| 3,827,305 | 8/1974 | Gilson et al. | 222/43 |
| 4,096,751 | 6/1978 | Withers et al. | 222/43 |

Primary Examiner—Joseph J. Rolla
Assistant Examiner—R. Stormer

[57] ABSTRACT

An adjustable volume dispenser comprises a barrel assembly having an internally threaded tubular portion, an adjustable stop formed with external threads engaged with the internal threaded tubular portion of said assembly, and a sleeve coaxially mounted within the tubular portion and rotatable therein, said sleeve being connected to the adjustable stop for imparting rotation thereto but allowing said stop to move axially thereon. A finger engageable wheel connects to the sleeve for rotating the adjustable stop relative to the barrel assembly, a plurality of numbered wheels being coaxially connected to the finger engageable wheel for indicating the position of the stop and the volume of liquid to be dispensed. A plunger assembly is provided including a rod reciprocally removeable within the barrel assembly, said rod extending coaxially through the adjustable stop, the sleeve and said wheels. The rod carries a fixed stop which cooperates with the adjustable stop, limiting the reciprocating throw of the plunger assembly.

7 Claims, 5 Drawing Figures

ADJUSTABLE VOLUME LIQUID DISPENSER

This invention relates generally to liquid dispensers and particularly to hand held dispensers having means for adjusting the throw of the plunger assembly with a digital read out of the volume set for dispensing. Devices of this general kind are known as exemplified by the teaching in U.S. Pat. No. 3,613,952.

In brief, the present invention is directed to an improvement in adjustable volume dispensers and more especially to a unique arrangement and combination of elements for adjusting the reciprocating throw of a plunger element.

The dispenser disclosed herein comprises a barrel assembly including an internally threaded tubular portion, an adjustable stop having interrupted external threads engaged with the internally threaded tubular portion, and a sleeve coaxially mounted within the tubular portion and rotatable therein, said sleeve being adapted for imparting rotation to the stop but allowing said stop to move axially thereon. A finger engageable wheel is provided for rotating the sleeve and stop relative to the barrel assembly. In the preferred embodiment, the sleeve is formed with a pair of elongate slots, the interrupted external threads of the adjustable stop projecting through said slots and engaged with the internally threaded tubular portion of the barrel assembly.

A digital read out is provided by a plurality of number wheels coaxially connected to the finger engageable wheel and moveable therewith. Means are provided for locking the finger engageable wheel in a set position of rotation while the plunger rod is being reciprocated within the barrel assembly. More particularly, the finger engageable wheel is formed with a plurality of peripheral recesses formed at equal radial distances from the rotational axis and angularly spaced apart equal angular distance around the wheel. The locking means comprises a detent engageable with the recesses for retaining the finger engageable wheel at any one of a plurality of positions of rotational adjustment.

One object of the invention is to provide a liquid volume dispenser having an improved means for adjusting the throw of a plunger assembly and, thus, adjusting the volume of liquid to be dispensed.

Another object of the invention is to provide an adjustable volume dispenser of the kind described including a plurality of numbered wheels for digitally indicating the volume to be dispensed.

A still further object is to provide an adjustable volume dispenser of the kind described including means for locking a finger engageable wheel in a set position of rotation while the plunger rod is being reciprocated within the barrel assembly.

Other objects of the present invention will become apparent in view of the following detailed description and the accompanying drawings.

In the drawings forming a part of this application and in which like parts are identified by like reference numerals throughout the same, FIG. 1 is a perspective view of a perferred embodiment of the invention in a liquid dispensing device;

Figure 1:
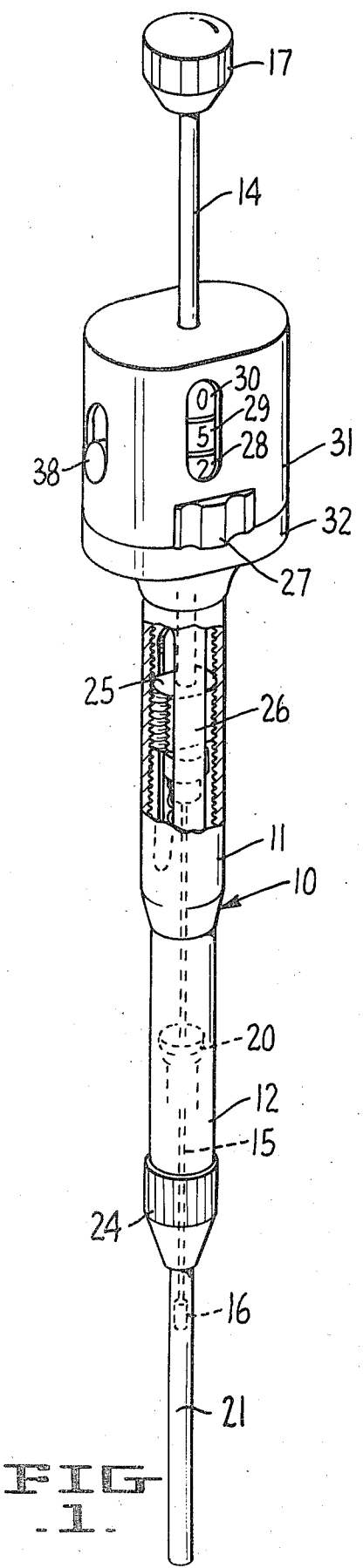
Figure 2:
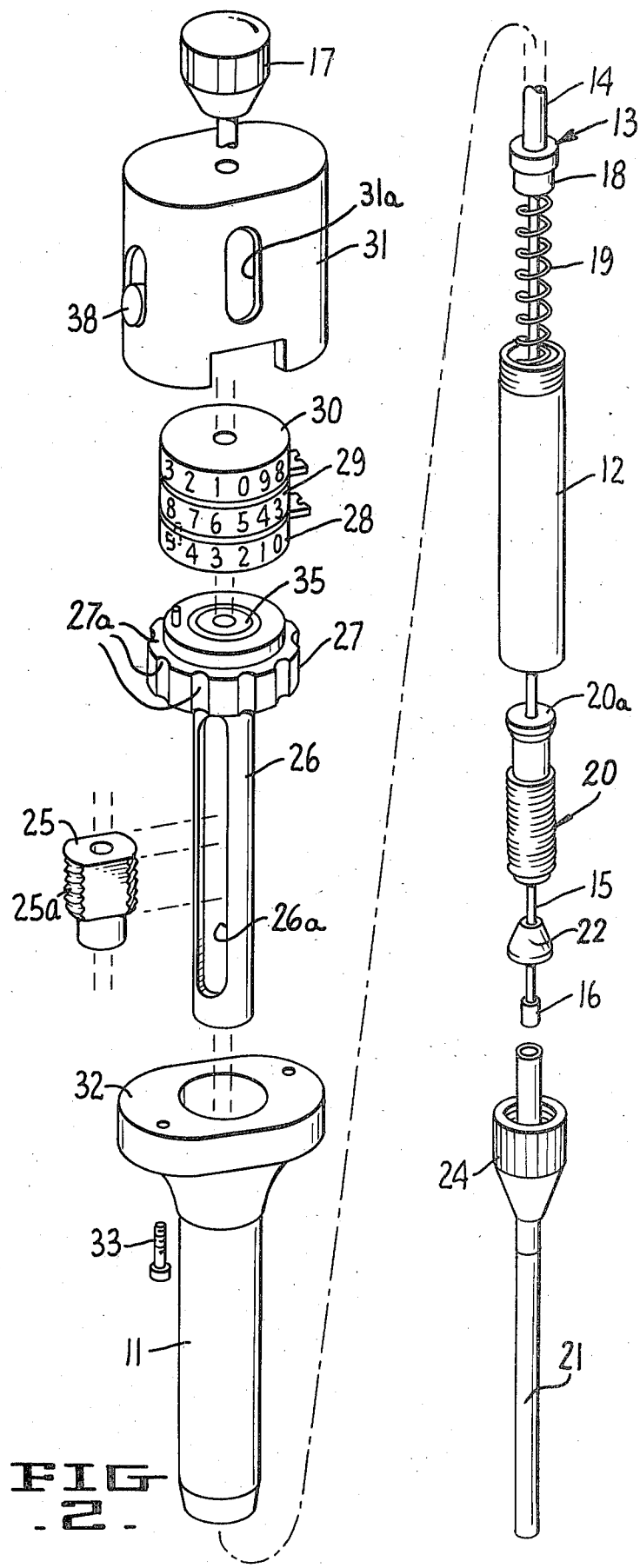
FIG. 2 is an exploded perspective view of the preferred embodiment showing various parts of the assembly.

The preferred embodiment illustrated comprises an elongate barrel assembly 10 consisting of an upper internally threaded tubular portion 11 and a lower tubular member 12 threadably connected thereto. A plunger assembly 13 is reciprocally mounted within the barrel assembly, said plunger assembly consisting of a plunger rod 14, a plunger wire 15 and a plunger tip 16. In addition, a finger engageable button 17 is mounted on the upper end of rod 14 and a spring seat and stop 18 is secured to the lower end of rod 14. The plunger assembly as a whole is resiliently biased and moved upwardly in the barrel assembly by a spring 19 seated between spring seat and contact 18 and a lower seat 20a formed on the end of a barrel closure plug 20. A portion of the closure plug is externally threaded and engageable with the internal threads of lower tubular portion 12. Plug 20 carries a capillary tube 21, and provides seats for a capillary retainer 22 and a stop 23. The capillary retainer and stop are held within the lower end of plug 21 by a collette 24. The structural relationships between the plunger assembly and the lower end of the barrel assembly are essentially the same as that described and shown in U.S. Pat. No. 4,098,125.

Figure 3:
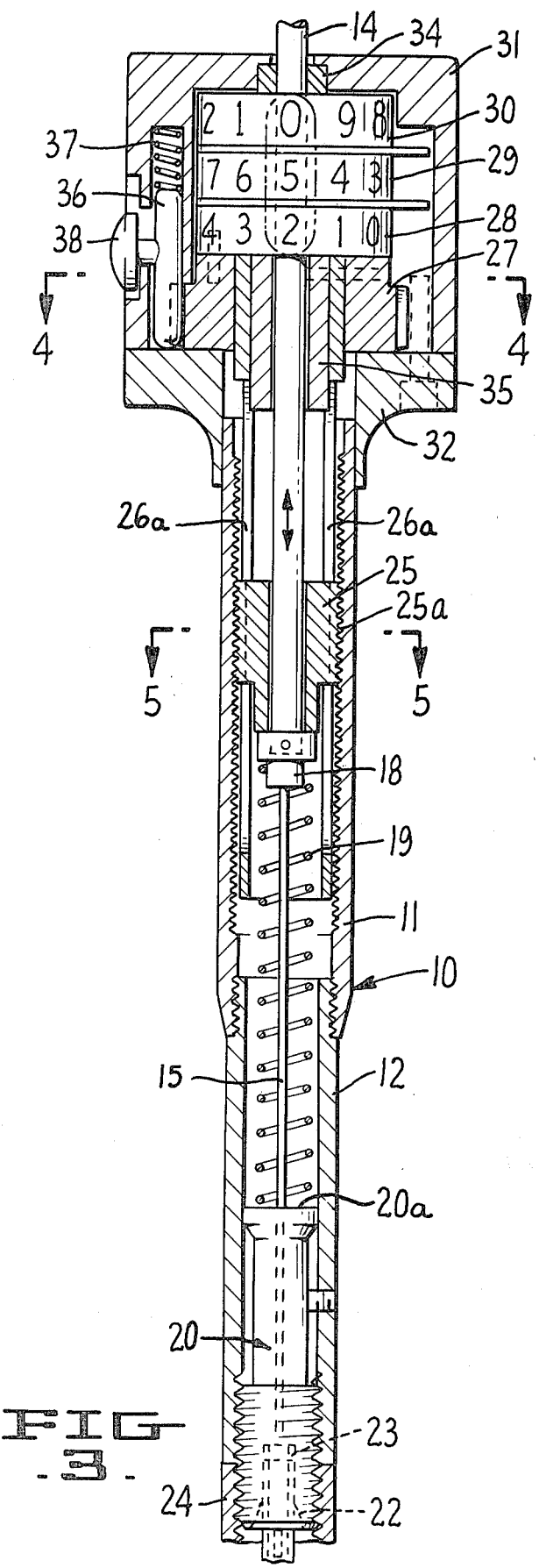
FIG. 3 is a longitudinal section of the dispenser.
Figure 4:
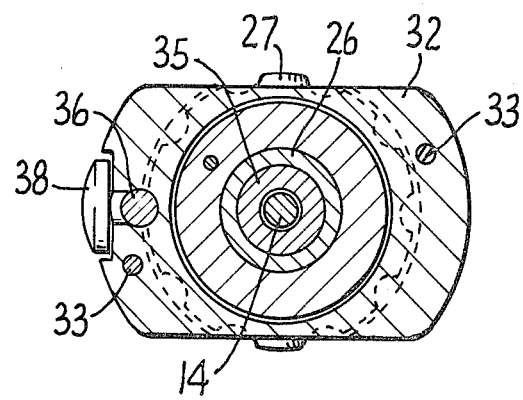
FIG. 4 is a transverse section taken on the lines 4—4 of FIG. 3.
Figure 5:
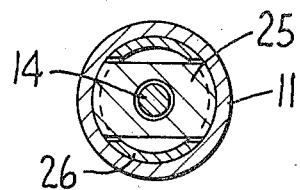
FIG. 5 is a transverse section taken on the lines 5—5 of FIG. 3.

This invention more particularly relates to the manner in which the reciprocating throw of the plunger assembly is limited or controlled to adjust the volume of liquid dispensed. In that regard an adjustable stop 25 is provided within tubular barrel 11, said stop having external interrupted threads 25a threadably engaged with the internal threads of tubular portion 11. A sleeve 26 having a pair of elongate slots 26a provides means for imparting rotation to the stop while allowing the stop to move axially therealong. As shown in FIG. 3, the external interrupted threads of stop 25 project through the elongate slots of sleeve 26 to engage the internally threaded tubular portion 11 of barrel assembly 10. Rotation of sleeve 26 brings the edges of slotted openings 26a into contact with stop 25, thereby rotating the stop. The threaded engagement between stop 25 and tubular barrel 11 forces the stop to move axially as a function of threaded lead and sleeve rotation.

A finger engageable wheel 27 coaxially connects to sleeve 26; and means are provided which indicate the axial position of the adjustable stop, said means comprising a plurality of number wheels 28, 29 and 30 which are connected to and driven by finger engageable wheel 27 in the known manner and customary construction of a multiple digit counter. Finger engageable wheel 27 and numbered wheels 28, 29 and 30 are housed within an elongated cylindrical shell 31 and supported on a body 32, shell 31 and body 32 being held together by a pair of connecting bolts 33. A window 31a formed in shell 31 allows the number wheels to be read. An upper guide sleeve 34 and a lower guide sleeve 35 provide means for centering plunger shaft 14 relative to shell housing 31, sleeve 26 and body 32.

Means are also provided for locking finger engageable wheel 27 in a set position of rotation while plunger rod 14 is reciprocated within barrel assembly 10. For this purpose wheel 27 is formed with a plurality of peripheral recesses 27a, said recesses being formed at equal radial distances from the rotational axis of the wheels and angularly spaced apart equal angular distances around the wheel. A detent 36 lodged within a cavity formed in shell 31, is urged into engagement with a recess of wheel 27 by a spring 37. Detent 36 may be withdrawn from engagement with a recess of wheel 27 (against the bias of spring 37) by finger contact and movement of a button 38 attached to detent 36.

In the preferred embodiment, finger engageable wheel 27 is formed with ten peripheral recesses. This is based on the decimal numbering system for which a plurality of complementary number wheels are adapted. The recesses 27a are, therefore, angularly spaced apart approximately 36° around the wheel and detent 36 is engageable with any of the recesses for retaining the wheel at any one of ten positions of rotational adjustment. It will be readily apparent that the volume of dispensing is directly proportional to axial movement of the plunger assembly. Since the internal bore of the capillary tube is essentially uniform, the distance of plunger movement may be callibrated directly into a volumetric measurement by proper selection of the lead in the threads 25a of adjustable stop 25 and the internal threads of tubular portion 11.

In operation, it will be noted, the axially throw or movement of plunger assembly 13 depends upon the position of adjustable stop 25. Contact between spring seat and stop 18 and the end of adjustable stop 25 determines the upper limit of travel of the plunger assembly. The lower limit of travel is determined by contact between the lower end of finger button 17 and the upper end of shell housing 31. An adjustment in the axial throw of plunger assembly 13 is made by simply rotating finger engageable wheel 27, thereby causing adjustable stop 25 to thread itself axially along and within tubular barrel portion 11 and sleeve 26. Rotation of finger engageable wheel 27 simultaneously causes a rotation of number wheels 28, 29 and 30.

Assuming that the number wheels are continuously numbered 0 through 9 (i.e., 0,1,2,3,4,5,6,7,8,9) a single revolution of finger engageable wheel 27 rotates wheel 28 one full rotation. In the process number wheel 29 will be advanced one number (one tenth of a rotation); and ten full revolutions of number wheel 29 will advance number wheel 30 one tenth of a revolution. With proper calibration each digital reading through window 31a will show the volume which can be dispensed with one full reciprocation of the plunger assembly.

Although a preferred embodiment of this invention has been illustrated and described, various modifications and changes may be resorted to without departing from the spirit of the invention or the scope of the appended claims, and each of such modifications and changes is contemplated.

What is claimed is:

1. An adjustable volume dispenser comprising: a barrel assembly including an internally threaded tubular portion, an adjustable stop having external threads engaged with said internally threaded tubular portion, a sleeve coaxially mounted and rotatable within said tubular portion, said sleeve being connected to said adjustable stop for imparting rotation thereto but allowing said stop to move axially thereon, said sleeve having a pair of elongate slots, said adjustable stop being disposed and carried within said sleeve, the external threads of said stop projecting through said pair of elongate slots to engage the internally threaded tubular portion of said barrel assembly;

a finger engageable wheel coaxially connected to said sleeve and rotatable relative to said barrel assembly;

a plunger assembly including a rod reciprocally movable within said barrel assembly, said rod extending coaxially through said adjustable stop and said sleeve, and means mounted to and carried by said plunger assembly for engaging said adjustable stop; and means for indicating the axial position of said adjustable stop within the tubular portion of said barrel assembly.

2. The adjustable volume dispenser of claim 1, said finger engageable wheel having a plurality of peripheral recesses formed at equal radial distances from the rotational axis thereof, said recesses being angularly spaced apart equal angular distances around said wheel, and further comprising a detent engageable with said recesses for retaining said finger engageable wheel at any one of a plurality of positions, of rotational adjustment.

3. The adjustable volume dispenser of claim 1, said means for indicating the axial position of said adjustable stop comprising a plurality of number wheels coaxially connected to said finger engageable wheel and movable therewith.

4. An adjustable volume dispensing device of claim 3, and further including means for locking said finger engageable wheel in a set position of rotation while said plunger rod is being reciprocated within said barrel assembly.

5. An adjustable volume dispenser having a barrel assembly, a plunger assembly mounted within said barrel assembly for axial reciprocation, a pair of engageable stops, one of said stops being mounted on said plunger assembly and movable therewith, the other stop being mounted within said barrel assembly for axial adjustment, and an improvement in means for axially adjusting the location of said other stop comprising: a finger engageable wheel mounted for rotation on the axis of plunger reciprocation, said wheel having a plurality of peripheral and elongate recesses formed at equal radial distances from the rotational axis thereof, said recesses being angularly spaced apart equal angular distances around said wheel, each recess extending parallel to the axis of plunger reciprocation and open at one end for receiving a detent; and a finger engageable detent mounted for reciprocating movement parallel to the axis of plunger reciprocation and engageable with an axially aligned recess of said wheel.

6. The adjustable volume dispenser of claim 5, said finger engageable wheel having 10 recesses formed at equal radial distances from the rotational axis thereof, said recesses being angularly spaced apart approximately 36° around said wheel and further comprising a detent engageable with said recesses for retaining said finger engageable wheel at any one of 10 positions of rotational adjustment.

7. The adjustable volume dispenser of claim 5, and further comprising means for digitally indicating the axial position of said adjustable stop and comprising a plurality of number wheels coaxially connected to said finger engageable wheel and moveable therewith.

* * * * *